(12) United States Patent
Debaun et al.

(10) Patent No.: US 8,911,801 B2
(45) Date of Patent: Dec. 16, 2014

(54) NATURAL PRESERVATIVE ALTERNATIVES AND COMPOSITIONS CONTAINING SAME

(71) Applicant: Woodcliff Skincare Solutions, Inc., Pittsburgh, PA (US)

(72) Inventors: Denise Debaun, New York, NY (US); Rose Hoyle, New York, NY (US); Shirley Weinstein, New York, NY (US)

(73) Assignee: Woodcliff Skincare Solutions, Inc., Pittsburgh, PA (US)

( * ) Notice: Subject to any disclaimer, the term of this patent is extended or adjusted under 35 U.S.C. 154(b) by 0 days.

(21) Appl. No.: 14/085,917

(22) Filed: Nov. 21, 2013

(65) Prior Publication Data

US 2014/0079819 A1    Mar. 20, 2014

Related U.S. Application Data

(63) Continuation of application No. 13/062,289, filed as application No. PCT/US2009/059344 on Oct. 2, 2009, now Pat. No. 8,623,430.

(60) Provisional application No. 61/195,316, filed on Oct. 6, 2008.

(51) Int. Cl.
| | | |
|---|---|---|
| *A01N 65/00* | (2009.01) | |
| *A61Q 19/00* | (2006.01) | |
| *A61K 8/97* | (2006.01) | |
| *A01N 37/44* | (2006.01) | |
| *A01N 35/06* | (2006.01) | |
| *A01N 65/08* | (2009.01) | |
| *A61K 8/34* | (2006.01) | |
| *A01N 31/02* | (2006.01) | |
| *A61K 8/35* | (2006.01) | |
| *A61K 8/44* | (2006.01) | |

(52) U.S. Cl.
CPC .............. *A01N 65/08* (2013.01); *A61K 2800/51* (2013.01); *A61Q 19/00* (2013.01); *A01N 65/00* (2013.01); *A61K 8/97* (2013.01); *A01N 37/44* (2013.01); *A01N 35/06* (2013.01); *A61K 2800/524* (2013.01); *A61K 8/345* (2013.01); *A01N 31/02* (2013.01); *A61K 8/35* (2013.01); *A61K 8/34* (2013.01); *A61K 8/44* (2013.01)
USPC ......................................................... 424/725

(58) Field of Classification Search
None
See application file for complete search history.

(56) References Cited

U.S. PATENT DOCUMENTS

| | | |
|---|---|---|
| 5,037,843 A | 8/1991 | Schoenberg |
| 5,965,594 A | 10/1999 | Schoenberg et al. |
| 2004/0213748 A1 | 10/2004 | Chuah et al. |
| 2005/0271595 A1 | 12/2005 | Brown |
| 2006/0018867 A1 | 1/2006 | Kawasaki et al. |
| 2007/0134284 A1 | 6/2007 | Parker |

FOREIGN PATENT DOCUMENTS

| | | |
|---|---|---|
| CN | 101273971 A | 10/2008 |
| EP | 683978 A1 | 11/1995 |
| FR | 2902290 A1 | 12/2007 |
| WO | 2006045743 A1 | 5/2006 |

OTHER PUBLICATIONS

International Report on Patentability and Written Opinion dated Apr. 21, 2011, received in Application No. PCT/US2009/059344.

*Primary Examiner* — Michael Meller
(74) *Attorney, Agent, or Firm* — Steven B. Kelber

(57) ABSTRACT

A cosmetic preservative is disclosed which comprises *Lonerica* sp. extract, a metal chelating agent and ethanol in amounts effective to inhibit microbial growth including bacteria, molds and yeast. The effectiveness may be enhanced by the addition of a phospholipid, ascorbic acid and ascorbic acid salts. Effectiveness against microbial growth is further improved by addition of a combination of 1,2-hexanediol, 1,2 octanediol and tropolone. Specific formulations are provided.

2 Claims, No Drawings

NATURAL PRESERVATIVE ALTERNATIVES AND COMPOSITIONS CONTAINING SAME

PRIORITY DATA AND INCORPORATION BY REFERENCE

This application is a continuation of application Ser. No. 13/062,289, filed Apr. 20, 2011, pending, which claims the benefit PCT Patent Application Serial Number PCT/US09/59344, filed Oct. 2, 2009, which claims priority under 35 U.S.C. §119(e) of U.S. Provisional Patent Application No. 61/195,316, filed on Oct. 6, 2008, which is incorporated by reference herein in its entirety.

BACKGROUND OF THE INVENTION

1. Field of the Invention

The present invention relates generally to novel natural preservative alternative systems (nPAS) and compositions containing same. The nPAS of the present invention are particularly suited for use in, inter cilia, natural, green, organic, sustainable, holistic, bio-degradeable, natureidentical homeopathic, eco-friendly, earth-friendly, environmentally safe, preservative-free, paraben-free and non-toxic products. And within those categories of products, the preservative alternatives of the present invention are particularly suited for use in, inter alia, personal care products, cosmetics, treatment, skin care and anti-aging products, cosmeceuticals, nutraceuticals, beauty foods, fragrance products, pharmaceuticals and food stuffs.

2. Related Art

This invention is related to the art of providing cosmetics with a preservative to suppress, in particular, microbiological growth on the cosmetics. While the preservatives of this invention can be used in virtually any cosmetic, this is particularly true of water-in-oil and oil-in-water preparations. They can be present as emulsions, gels or soft solids. Conventional lipsticks are examples of soft solids. Commonly employed preservatives include hydantoin derivatives and the family of compounds generally referred to as parabens. U.S. Pat. Nos. 5,037,843 and 5,965,594 are representative of patents I nthis field of cosmetic preservatives.

BACKGROUND OF THE TECHNOLOGY

The demand for organic/natural consumer products continues to increase world wide. This demand has paralleled the increasingly expansive recognition of the health benefits and environmental benefits of products falling into one or more of the categories including: natural, green, organic, sustainable, holistic, bio-degradeable, nature-identical, homeopathic, ecofriendly, earth-friendly, environmentally safe, preservative-free, paraben-free and non-toxic. For example, the natural & organic sector(s) has become one of the fastest growing in the North American personal care and cosmetics industries, with sales increasing by approximately 20% per year. Healthy market growth rates have been projected to increase the market share of natural & organic products at least 15-20% of the total sales for cosmetic & toiletry products in the coming years. Global sales of natural & organic cosmetics are rapidly increasing with some sources projecting projected revenues approaching US$7 billion in 2008.

Apart from an influx of new product launches, a major driver of market growth appears to be the mainstreaming of natural & organic products. Distribution in mainstream retailers is increasing as retailers react to market demand.

Increasing market demand and the absence of official standards have led to much consumer confusion within the marketplace as to what constitutes "natural" or "organic" products and the introduction of many pseudo-natural products. Nonetheless the proliferation of organic and natural personal care products is leading to increased consumer awareness and scrutiny of the ingredient composition. With this enhanced knowledge and understanding, the demand for products that contain increased concentrations of natural extracts, botanicals and ingredients derived from natural sources coupled with a reduction of (and if possible/practical, the elimination of) ingredients that are known or suspected health threats (e.g., pesticides, toxins, antibiotics, etc.). This consumer demand has recently led to the private sector establishment of ethical and certified organic ingredients. Indeed, a growing number of companies have recently initiated processes through which one can receive third-party certification of the "organic" character of products.

Similarly, exceptionally high market growth rates are pushing global organic food & drink sales towards US $40 billion per year. With demand outpacing supply, supply shortages have been experienced. Undersupply is most evident in the North American region where empty retailer shelves have become commonplace for some product categories. Several European countries are also experiencing supply shortages this year as consumer demand for organic foods has escalated.

Although there are very few consistent definitions for what constitutes "organic" or "natural," there is a clear market demand for products that do not include chemicals that are not essential to the product functioning or character of the products in question and, where required, that the specific ingredients be non-toxic, environmentally friendly, bio-degradable, naturally derived, organic and/or derived from sustainable resources when possible.

Preservatives perform a key function in modern manufacture, marketing and retailing. Most pharmaceuticals, foods, fragrance products, cosmeceuticals, nutraceuticals, cosmetics, treatment, skin care and anti-aging products, personal care products, etc., commonly contain ingredients that are capable of supporting microbial growth and proliferation. Additionally, regardless of their use, these types of products typically contain water as one of the primary components. This water provides a medium in which microorganisms can survive and/or proliferate. Thus, these products by their very nature create an environment and viable medium for the proliferation of microbial organisms. Without the addition of some preservative agent, these types of products are susceptible to microbial contamination and proliferation.

By way of a representative non-limiting example, personal care products such as cosmetics and skin care products typically contain ingredient(s) (i.e., preservatives) which inhibit, or otherwise limit, microbial proliferation thereby protecting the product from, for example, degradation/putrefaction. In addition, these ingredients serve to protect the consumer from problems attending microbial contamination. Thus, preservatives provide a benefit to the manufacturer (e.g., providing a longer sustainable shelf-life) and a benefit to the consumer (e.g., stable products, reduction of contamination and/or infection and consistent product performance).

Emulsion systems (for example, oil-in-water (o/w), water-in-oil (w/o», multiple emulsions (for example water-in-oil-in-water (w/o/w) and oil-in-water-in-oil (o/w/o) systems), liposomal systems and aqueous-based liquid, gel or suspension systems are the major product forms used for topical delivery systems in cosmetic, skin care, personal care, OTC pharmaceutical, ophthalmic, otic, dermatological and other prescription pharmaceutical products. Each of these delivery systems contains water, as well as ingredients that can support and/or sustain the growth of microorganisms such as bacteria, yeast and molds. These products therefore typically contain preservatives to kill or at least inhibit the growth of microorganisms, usually in amounts intended to provide efficacy while hopefully avoiding any adverse effect on the user. Government regulatory agencies commonly regulate the concentrations of the preservatives employed, doing so to protect the consumer by reducing the potential for, inter alia, irritation and/or allergic sensitization.

The increasing desire for natural and/or organic products creates and inherent conflict with the need to inhibit microbial growth and proliferation. Traditional and commonly employed preservative agents are, by their very nature, toxic. Some of the more commonly used preservatives in topically applied products include the following materials listed alphabetically according to their International Nomenclature for Cosmetic Ingredients (Na) name: Benzoic Acid (and salts), Benzyl Alcohol, 2-bromo-2-nitropropane-I,3-diol, Chlorhexidine, Chloroxylenol Dehydroacetic Acid (and salts), Diazolidinyl Urea, DMDM Hydantoin, Imidazolidinyl Urea, Isothazolinones, Paraben Esters, Phenethyl Alcohol, Phenoxyethanol and Quaternim-15.

The esters of p-hydrobenzoic acid are known as parabens, and include methyl, ethyl, propyl and butyl esters. Higher esters are even more active then the butyl esters, but decreasing solubility makes them less desirable to use. Benzoic acid may be used either as the acid, or as a salt such as sodium benzoate. There is an increasing consumer demand for products that do not contain paraben preservatives.

Formaldehyde has been another prominent and potent antimicrobial agent; other agents gradually donate or release formaldehyde. This category of preservatives includes, for example, imidazolidinyl urea, diazolidinyl urea, DMDM hydantion and Quatemim-15. Many of the topically applied products use either imidazolidinyl urea (Germall 115® from Sutton Labs) or diazolidinyl urea (Germall II® from Sutton Labs), alone or in combination with other agents such as parabens. Some countries, such as Japan, restrict the use of "formaldehydedonating" preservative agents, such as imidazolidinyl urea and diazolidinyl urea, and prohibit the use of "formaldehyde-releasing" preservative agents such as Quaternium-15 and DMDM Hydantoin. Other countries, such as the European Union, are not as restrictive about the types of preservative agents that can be employed, however, they limit the concentration of each agent included in a product. As with paraben compounds, there is an increasing consumer demand for products that do not contain formaldehyde donating/releasing preservatives.

The choice of preservative agents to incorporate into a product and/or formulation, and the amount of each agent required for efficacy, typically varies from one product/formulation to another. The effective amount is commonly determined empirically by preservative efficacy testing (e.g., storage studies, challenge tests, etc.). Despite the expertise and knowledge in the art of formulation, each combination of preservative agents and adjuvants used in a particular formulation should be tested for effectiveness against a broad range of microorganisms. This is because it is often not well understood why a particular combination of preservative agents and adjuvants will be effective within a given formulation, environment, etc. Moreover, given the potential for irritation and sensitization from preservative agents, an additional objective of the manufacturer/formulator is to create a preservative system that does not cause adverse reactions and/or complications.

An ideal preservative system has a broad-spectrum of activity against all types of microorganisms, including yeast and mold, and gram-positive and gram-negative bacteria. The preservative is also ideally effective at low concentrations, to minimize expense and avoid irritation and/or sensitization reactions. The ideal preservative should exhibit a good solubility profile in both oil and water phases of an emulsion to ensure that the preservative is present in that portion of the product where it can be effectively assimilated by the microorganisms.

The preservative should also be compatible with the other ingredients in the formulation, and not react with or otherwise be inactivated by those ingredients. The preservative is ideally colorless and odorless, and remains so throughout the intended shelf-life of the product. It should also be stable throughout the expected life of the product, because many microorganisms can lay dormant in the composition until conditions are later appropriate for growth. If a preservative was unstable and degraded over the shelf-life of the product, contamination could occur once the preservative concentration fell below the threshold necessary to inhibit the growth of the microorganisms. Furthermore, the preservative is ideally stable to any changes in temperature and/or pH encountered during the manufacturing and packaging process, as well as the storage conditions encountered both prior to and after sale to the end user.

The preservative should also be safe, without exerting undesired biological effects on human skin cells. Even at typical use concentrations, many preservatives have the capacity to cause irritation and/or sensitization. Furthermore, since the concentrated preservative agents must be handled and incorporated into the product during the manufacturing process, these materials must not present an insurmountable hazard to the production workers during the manufacture/formulation processes.

The preservative agents are preferably easy to handle in their bulk state, prior to incorporation into a formulation, and inexpensive to use. More expensive preservatives are ideally effective at lower concentrations for cost effectiveness criteria.

No single preservative agent fulfills all of these criteria, and the requirements become even more complex when regulatory requirements are added to the criteria, and entirely unmet with respect to the natural/organic requirement. Formulation scientists working in collaboration with microbiologists and analytical chemists continue to expend a significant amount of effort in developing adequate preservative systems in an attempt to satisfy both practical and regulatory requirements.

Developing a novel, safe, naturally derived I organic, and internationally acceptable preservative alternative is a complex problem that has been addressed by the present invention. The following description of the preservative alternative is meant to be representative of the overall technology. Anyone skilled in the art of formulation and/or microbiology will see variations and potential applications for this technology beyond the examples provided herein. Therefore, the present invention is not limited to the examples or specific formulations represented by these examples, but instead it will be understood that the examples and explanations disclosed herein are provided only for illustrative purposes and that in view of the instant disclosure, various modifications of the present invention will be apparent to those skilled in the art and are to be included within the spirit and purview of this application and the scope of the appended claims.

SUMMARY OF THE INVENTION

The present invention relates to preservative alternatives that exhibit anti-microbial activities and compositions containing same. For ease of reference, the natural preservative alternative systems may be referred to herein as "nPAS".

The nPAS of the present invention are particularly suited for use in, inter alia, natural, green, organic, sustainable, holistic. bio-degradeable, nature-identical, homeopathic, ecofriendly, earth-friendly, environmentally safe, preservative-free, paraben-free and non-toxic products. And within those categories of products, the preservative alternatives of the present invention are particularly suited for use in, inter alia, personal care products, cosmetics, treatment, skin care and anti-aging products, cosmeceuticals, nutraceuticals, fragrance products, pharmaceuticals and food stuffs. Thus, the present invention provides a significant advancement and improvement over the preservative systems used in the above-identified applications, products and or markets.

The nPAS of the present invention comprise an effective amount of (a) *Lonicera* sp. flower extract, (b) a metal-chelating agent, and (c) ethyl alcohol.

The *Lonicera* sp. flower extract is from one or more members of the group consisting of *Lonicera caprifolium* and *Lonicera japonica*. In a preferred embodiment, the extract is a mixture of the extracts from both species. A particular feature of the claimed invention is that it employs only biodegradable and eco-friendly components that are widely available in high purity (cosmetic grade) formulations. The *Lonicera* pant family is comprised of the two main species, and has been used as a medicinal herb, particularly in alternative medicine, for thousands of years. It is reputed to have qualities as an anti-pyretic abd an effective agent in the treatment of inflammation. It has been used in formulations to treat upper respiratory disease infections. It is generally available as an ethanol based extraction, from a wide variety of sources, including Huzhou N.B,C. Biological Material Co. of China. Ethyl alcohol, or ethanol, is universally ailable as a solvent. Metal chelating agents are also widely available. A family of chelating agents is sold under the mark Dissolvine by Akzo Nobel.

For purposes of the present invention, the use of the word natural is intended to encompass each of the categories including: natural, green, organic, sustainable, holistic. biodegradeable, nature-identical, homeopathic, eco-friendly, earth-friendly, environmentally safe, preservative-free, paraben-free and non-toxic; and shall not, unless otherwise specifically delineated, be limited in any manner to exclude any of the foregoing categories.

In view of the many possible embodiments to which the principles of our invention may be applied, it should be recognized that the illustrated embodiments are only some examples of the invention and should not be taken as a limitation on the scope of the invention.

Among the preferred embodiments of the present invention are natural preservative alternatives for use in topically applied cosmetics and skin care products. This preservative alternative of the present invention not only provide significant protection from the potential of microbial contamination and proliferation, but also reduce the risk of irritation or sensitization associated with the preservative systems found in many person care products.

DETAILED DESCRIPTION

The present invention relates generally to a novel natural preservative alternative systems that exhibit effective anti-microbial activity and composition containing same. While the novel organic anti-microbial preservatives of the present invention are particularly suited for use in, inter alia, pharmaceuticals, foods, cosmeceuticals, neutriceuticals, cosmetics, treatment, skin care and anti-aging products, fragrance products and personal care products (collectively "Applications" without limitation), the claims of this application focus on the development of preservatives and anti-microbial formulations for addition to cosmetic, and the resulting cosmetics. The present invention involves several new combinations of agents that have been identified that not only exhibit significant antimicrobial efficacy, but simultaneously have been shown to be safe in use.

These preservative alternative combinations are also acceptable to regulatory agencies in many jurisdictions, for example the U.S., European Economic Community and Japan, and are effective against gram positive and gram negative bacteria, yeast and molds. In particular, the claimed nPAS are effective against those organisms typically tested for in challenge tests: *S. aureus, E. coli, P. vulgaris, E. cloacae, E. gergoviae, P. aeruginosa, P. flourescens, P. cepacia, Flavobacterium* sp., *A. niger, C. albicans, Penicillium* sp., *P. decumbens* and *Trichoderma* sp.

The nPAS of the present invention comprise an amount of (a) *Lonicera* sp. flower extract, (b) a metal-chelating agent, and (c) ethyl alcohol effective to be intimately blended with the cosmetic it is to be added to, and inhibit microbial, particularly bacterial, growth in or on the cosmetic.

The *Lonicera* sp. flower extract is from one or more members of the group consisting of *Lonicera caprifolium* and *Lonicera japonica*. In a preferred embodiment, the extract is a mixture of the extracts from both species.

In a preferred embodiment, the nPAS is formulated such that in relation to the composition to which it will be added, comprises by weight measure: (a) 0.1-5% of *Lonicera* sp. flower extract, (b) 0.1-6% L-glutamic acid N,N-diacteic acid, tetra sodium salt ("GLDA") and (c) 1-10% ethyl alcohol.

In a more preferred embodiment, the nPAS is formulated such that in relation to the composition to which it will be added, comprises: (a) 0.25-3% of *Lonicera* sp. flower extract, (b) 0.1-2% L-glutamic acid N,N-diacteic acid, tetra sodium salt ("GLDA") and (c) 2-6% ethyl alcohol.

In a more preferred embodiment, the nPAS is formulated such that in relation to the composition to which it will be added, comprises: (a) 1-2% of *Lonicera* sp. flower extract, (b) 0.1-0.25% L-glutamic acid N,N-diacteic acid, tetra sodium salt ("GLDA") and (c) 3-5% ethyl alcohol.

In a preferred embodiment, a nPAS for topical skin cream is formulated such a the topical skin cream composition comprises: (a) 1% of *Lonicera* sp. flower extract, (b) 0.1-0.2% L-glutamic acid N,N-diacteic acid, tetra sodium salt ("GLDA") and (c) 5% ethyl alcohol.

In a more preferred embodiment, a nPAS for topical skin cream is formulated such that the topical skin cream composition comprises: (a) 1% of *Lonicera* sp. flower extract, (b) 0.1125% Lglutamic acid N,N-diacteic acid, tetra sodium salt ("GLDA") and (c) 5% ethyl alcohol.

In a preferred embodiment, a nPAS for topical skin serum is formulated such a the topical skin serum composition comprises: (a) 1% of *Lonicera* sp. flower extract, (b) 0.1-0.2% Lglutamic acid N,N-diacteic acid, tetra sodium salt ("GLDA") and (c) 3% ethyl alcohol.

In a more preferred embodiment, a nPAS for topical skin serum is formulated such a the topical skin serum composition comprises: (a) 1% of *Lonicera* sp. flower extract, (b) 0.1125% Lglutamic acid N,N-diacteic acid, tetra sodium salt ("GLDA") and (c) 3% ethyl alcohol.

Particularly useful enhancers of antimicrobial activity have been found to be phospholipids in a concentration sufficient to enhance an antimicrobial action of the composition; ascorbic acid or one or more of its salts in a concentration sufficient to enhance an antimicrobial action of the composition; and/or a combination of two or more members selected from the group consisting of 1,2-hexanediol, 1,2-octanediol and one or more tropone compounds. When present, the phospholipid (such as Phospholipid COM) should be added such that in the final product to which it is applied, the concentration is within the range of about 0.5 to 2%, the ascorbic acid or its salt is present in a concentration range of about 0.2-5%, and the one or more members of the group consisting of 1,2-hexanediol, 1,2 octanediol and one or more tropone compound is present in a concentration of about 0.1-5%. In a preferred embodiment, the tropone compound is 2, hydroxy-2,4,6-cyclopentatriene-1-one (tropolone). A preferred mixture of 1,2 hexanediol, 1,2-octanediol and tropolone is commercially available as Sym-Diol68T (Symrise of Germany).

The natural preservative alternative systems of the present invention may be used in a wide variety of personal care, and in particular cosmetic, products for topical application including, inter alia, oil-in-water emulsions, water-in-oil emulsions, water-based formulations, water-based formulation containing high levels of surfactants, oil-based formulations, oil-based formulation containing high levels of surfactants, and liposomal suspensions, among others. Varying formulations of the preservative alternative systems of the present invention have been found to be particularly suited for these types of compositions, as explained in the following detailed description and/or readily understood by persons of ordinary skill in the relevant art(s).

It will be understood that the examples and explanations set forth herein are provided for illustrative purposes only and that in view of the instant disclosure, various modifications of the present invention will be apparent to those skilled in the art and are to be included within the spirit and purview of this application and the scope of the appended claims.

Example I

Skin Cream

The nPAS of the present invention is added to a natural cream containing water, Caprylic/Capric Triglyceride (2-8%), Alcohol (3-5%), Glycerin (1-3%), *Olea Europaea* (Olive) Fruit Oil (1-3%), Cetearyl Alcohol (1-3%), Glyceryl Stearate (1-3%), Hydrogenated Vegetable Oil (13%), *Simmondsia Chinensis* (Jojoba) Seed Oil (1-3%), Steareth-2 (1-3%), *Cocos Nucifera* (Coconut) Oil (1-3%), *Prunus Amygdalus Dulcis* (Sweet Almond) Oil (0.25-1%), Macadamia, Ternifolia Seed Oil (0.25-1%), Potassium Palmitoyl Hydrolyzed Wheat Protein (0.25-1%), *Linum Usitatissimum* (Linseed) Seed Oil (0.25-1%), Steareth-21 (0.25-1%), *Butyrospermum Parkii* (Shea Butter) (0.25-1%), *Cucumis Sativus* (Cucumber) Fruit Extract (0.25-1%), Moros Alba Fruit Extract (0.25-1%), *Camellia Sinensis* Leaf Extract (0.1-1%), *Glycyrrhiza Glabra* (Licorice) Root Extract (0.1-1%), *Ficus Carica* (Fig) Fruit Extract (0.1-1%), *Lonicera Caprifolium* (Honeysuckle) Flower Extract (0.1-0.5%), *Lonicera Japonica* (Honeysuckle) Flower Extract (0.1-0.5%), Palm Glycerides (0.1-0.5%), Potassium Lauroyl Wheat Amino Acids (0.10.5%), Sodium Chloride (0.1-0.5%), *Aloe Barbadensis* Leaf Extract (Alasta™) (0.1-0.5%), Canola Oil (0.1-0.5%), *Arriba Rosaeodora* (Rosewood) Wood Oil (0.1-0.5%), *Pelargonium Graveolens* Flower Oil (0.1-0.5%), *Citrus Aurantium Bergamia* (Bergamot) Fruit Oil (0.1-0.5%), *Pogostemon Cablin* Oil (0.1-0.5%), *Lavandula Angustifolia* (Lavender) Oil (0.1-0.5%), *Cananga Odorata* Flower Oil (0.1-0.5%), *Picea Mariana* Leaf Oil (0.1-0.5%), *Eugenia Caryophyllus* (Clove) Flower Oil (0.1-0.5%), *Vetiveria Zizanoides* Root Oil (0.1-0.5%), *Piper Nigrum* (Pepper) Fruit Oil (0.1-0.5%), *Citrus Medica Limonum* (Lemon) Peel Oil (0.1-0.5%), *Ocimum Basilicum* (Basil) Oil (0.1-0.5%), *Peucedanum Graveolens* (Dill) Extract (0.1-0.5%), *Foeniculum Vulgare* (Fennel) Oil (0.1-0.5%), *Mentha Piperita* (Peppermint) Oil (0.1-0.5%), Silica (0.1-0.5%), Xanthan Gum (0.1-0.5%), Bentonite (0.1-0.5%), Caproyl Glycine (0.10.5%), Tetrasodium Glutamate Diacetate (0.1-0.5%), Sodium Hydroxide (as required for pH adjustment).

The final concentration of the nPAS is added such that the components are present in the following amounts: (a) 1% of *Lonicera* sp. flower extract, (b) 0.1125% L-glutamic acid N,Ndiacteic acid, tetra sodium salt ("GLDA") and (c) 5% ethyl alcohol.

The nPAS is effective in prevention of microbial growth when tested in standard challenge tests for organisms including, e.g., *S. aureus, E. coli, P. vulgaris, E. cloacae, E. gergoviae, P. aeruginosa, P. jlourescens, P. cepacia, Flavobacterium* sp., *A. niger, C. albicans, Penicillium* sp., *P. decumbens* and *Trichoderma* sp.

Example II

Skin Serum

The nPAS of the present invention is added to a natural cream containing: Water, Alcohol (3-5%), Glycerin (1-3%), Maltodextrin (1-3%), *Aloe Barbadensis* Leaf Extract (Alasta™) (0.25-1%), *Glycine Soja* (Soybean) Oil (0.25-1%), *Citrus Aurantium Dulcis* (Orange) Oil (0.1-1%), *Eugenia Caryophyllus* (Clove) Leaf Oil (0.1-1%), *Citrus Medica Limonum* (Lemon) Peel Oil (0.1-1%), *Cymbopogon Martini* Oil (0.1-1%), *Ocimum Basilicum* (Basil) Oil (0.1-1%), *Lavandula Angustifolia* (Lavender) Oil (0.1-1%), *Salvia* Scl area (Clary) Oil (0.1-1%), *Eucalyptus Globulus* Leaf Oil (0.1-1%), *Vetiveria Zizanoides* Root Oil (0.1-1%), *Oryza Sativa* (Rice) Extract (0.1-1%), *Camellia Sinensis* Leaf Extract (0.1-1%), *Aspalathus Linearis* Leaf Extract (0.1-1%)" Xanthan Gum (0.1-1%), Pectin (0.1-0.5%), Tetrasodium Glutamate Diacetate (0.1-1%), Polyglyceryl-4 Caprate (0.1-1%), *Lonicera Caprifolium* (Honeysuckle) Flower Extract, *Lonicera Japonica* (Honeysuckle) Flower Extract (0.1-1%), Citric Acid (as required to adjust pH).

The final concentration of the nPAS is added such that the components are present in the following amounts: (a) 1% of *Lonicera* sp. flower extract, (b) 0.1125% L-glutamic acid N,Ndiacteic acid, tetra sodium salt ("GLDA") and (c) 3% ethyl alcohol.

The nPAS is effective in prevention of microbial growth when tested in standard challenge tests for organisms including, e.g., *S. aureus, E. coli, P. vulgaris, E. cloacae, E. gergoviae, P. aeruginosa, P. jlourescens, P. cepacia, Flavobacterium* sp., *A. niger, C. albicans, Penicillium* sp., *P. decumbens* and *Trichoderma* sp.

This invention has been described by generic reference, as well as being illustrated by specific embodiments. Within the parameters given, the adjustment of relative amounts, measured by weight or otherwise, will be within the sill of the ordinary artisan. Certain combinations will provide better protection against certain types of microbial colonization of the cosmetic to be prepared, while others may give superior moisturizing effect of their own. Selection there between, unless specifically recited in the appended claims, does not rise to the level of invention and can be arrived at by those of skill in the art following the teachings of this application.

What is claimed is:

1. A lipstick comprising, in percent by weight, Caprylic/CapricTriglyceride (2-8%), Alcohol (3-5%), Glycerin (1-3%), Olea Europaea (Olive) Fruit Oil (1-3%), Cetearyl Alcohol (1-3%), Glyceryl Stearate (1-3%), Hydrogenated Vegetable Oil (1-3%), *Simmondsia Chinensis* (Jojoba) Seed Oil (1-3%), Steareth-2 (1-3%), *Cocos Nucifera* Oil (1-3%), *Prunus Amygdalus* Dulcis Oil (0.25-1%), *Macadamia, Ternifolia* Seed Oil (0.25-1%), Potassium Palmitoyl Hydrolyzed Wheat Protein (0.25-1%), *Linum Usitatissimum* Seed Oil (0.25-1%), Steareth-21 (0.25-1%), *Butyrospermum Parkii* (0.25-1%), *Cucumis Sativus* Fruit Extract (0.25-1%), *Moros Alba* Fruit Extract (0.25-1%), *Camellia Sinensis* Leaf Extract (0.1-1%), *Glycyrrhiza Glabra* Root Extract (0.1-1%), *Ficus Carica* Extract (0.1-1%), *Lonicera Caprifolium* Flower Extract (0.1-0.5%), *Lonicera Japonica* Flower Extract (0.1-0.5%), Palm Glycerides (0.1-0.5%), Potassium Lauroyl Wheat Amino Acids (0.10.5%), Sodium Chloride (0.1-0.5%), *Aloe Barbadensis* Leaf Extract (0.1-0.5%), Canola Oil (0.1-0.5%), Arriba Rosaeodora Wood Oil (0.1-0.5%), *Pelargonium Graveolens* Flower Oil (0.1-0.5%), Citrus *Aurantium* Bergamia Fruit Oil (0.1-0.5%), Pogostemon Cablin Oil (0.1-0.5%), *Lavandula Angustifolia* Oil (0.1-0.5%), *Cananga Odorata* Flower Oil (0.1-0.5%), *Picea Mariana* Leaf Oil (0.1-0.5%), *Eugenia Caryophyllus* Flower Oil (0.1-0.5%), *Vetiveria Zizanoides* Root Oil (0.1-0.5%), *Piper Nigrum* (Pepper) Fruit Oil (0.1-0.5%), Citrus Medica Limonum Peel Oil (0.1-0.5%), *Ocimum Basilicum* Oil (0.1-0.5%), *Peucedanum Graveolens* Extract (0.1-0.5%), *Foeniculum Vulgare* Oil (0.1-0.5%), *Mentha Piperita* Oil (0.1-0.5%), Silica (0.1-0.5%), Xanthan Gum (0.1-0.5%), Bentonite (0.1-0.5%), Capryloyl Glycine (0.10.5%), Tetrasodium Glutamate Diacetate (0.1-0.5%), with the balance water, adjusted for a pH for topical administration by the addition of sodium hydroxide.

2. A lipstick comprising, in amounts by percent by weight, Ethanol (3-5%), Glycerin (1-3%), Maltodextrin (1-3%), *Aloe Barbadensis* Leaf Extract (0.25-1%), *Glycine Soja* Oil (0.25-1%), Citrus *Aurantium Dulcis* Oil (0.1-1%), *Eugenia Caryophyllus* Leaf Oil (0.1-1%), Citrus Medica Limonum Peel Oil (0.1-1%), *Cymbopogon Martini* Oil (0.1-1%), *Ocimum Basilicum* Oil (0.1-1%), *Lavandula Angustifolia* Oil (0.1-1%), *Salvia Sclarea* Oil (0.1-1%), *Eucalyptus Globulus* Leaf Oil (0.1-1%), *Vetiveria Zizanoides* Root Oil (0.1-1%), *Oryza Sativa* Extract (0.1-1%), *Camellia Sinensis* Leaf Extract (0.1-1%), *Aspalathus Linearis* Leaf Extract (0.1-1%)" Xanthan Gum (0.1-1%), Pectin (0.1-0.5%), Tetrasodium Glutamate Diacetate (0.1-1%), Polyglyceryl-4 Caprate (0.1-1%), *Lonicera Caprifolium* (Honeysuckle) Flower Extract, *Lonicera Japonica* (Honeysuckle) Flower Extract (0.1-1%), the balance water, the pH adjusted for topical administration with citric acid.

* * * * *